US007432944B2

(12) United States Patent
Flotats et al.

(10) Patent No.: US 7,432,944 B2
(45) Date of Patent: Oct. 7, 2008

(54) ILLUMINATION UTILIZING A PLURALITY OF LIGHT SOURCES

(75) Inventors: Carles Flotats, Barcelona (ES); Jose M Rio Doval, Sant Cugat del Valles (ES); Rodrigo Ruiz, Terrassa (ES); Marcos Casaldaliga, Sant Cugat del Valles (ES)

(73) Assignee: Hewlett-Packard Development Company, L.P., Houston, TX (US)

( * ) Notice: Subject to any disclaimer, the term of this patent is extended or adjusted under 35 U.S.C. 154(b) by 223 days.

(21) Appl. No.: 11/235,582

(22) Filed: Sep. 26, 2005

(65) Prior Publication Data

US 2006/0092209 A1 May 4, 2006

(30) Foreign Application Priority Data

Oct. 28, 2004 (EP) ................................. 04105368

(51) Int. Cl.
*B41J 2/435* (2006.01)

(52) U.S. Cl. ........................................ 347/236; 347/246

(58) Field of Classification Search ......... 347/128–133, 347/236–238, 244, 246–249, 116, 229, 234; 315/169.3
See application file for complete search history.

(56) References Cited

U.S. PATENT DOCUMENTS

| | | | |
|---|---|---|---|
| 5,105,207 A | 4/1992 | Nelson | |
| 5,151,718 A | 9/1992 | Nelson | |
| 5,159,485 A | 10/1992 | Nelson | |
| 5,365,084 A | 11/1994 | Cochran et al. | |
| 5,686,720 A | 11/1997 | Tullis | |
| 5,856,833 A | 1/1999 | Elgee et al. | |
| 5,954,424 A | 9/1999 | Anderson et al. | |
| 6,011,575 A * | 1/2000 | Haneda | 347/238 |
| 6,188,427 B1 | 2/2001 | Anderson et al. | |
| 6,266,137 B1 | 7/2001 | Morinaga | |
| 6,291,829 B1 | 9/2001 | Allen et al. | |
| 6,366,350 B1 | 4/2002 | Thornburg et al. | |
| 6,408,156 B1 * | 6/2002 | Miyazaki et al. | 399/301 |
| 6,530,666 B1 | 3/2003 | Smith et al. | |
| 6,561,613 B2 | 5/2003 | Cunnagin et al. | |
| 6,599,042 B2 | 7/2003 | Wolf | |
| 6,624,880 B2 | 9/2003 | Sandstrom et al. | |
| 6,633,301 B1 | 10/2003 | Dallas et al. | |
| 6,642,492 B2 | 11/2003 | Shiota et al. | |
| 6,724,379 B2 | 4/2004 | Markis | |
| 6,788,323 B2 | 9/2004 | Enomoto et al. | |
| 6,945,721 B2 * | 9/2005 | Sato | 400/708 |
| 7,034,858 B2 * | 4/2006 | Oba et al. | 347/237 |
| 2001/0042847 A1 | 11/2001 | Eisen | |
| 2004/0114028 A1 * | 6/2004 | Takeuchi et al. | 347/244 |
| 2004/0183457 A1 * | 9/2004 | Kondo et al. | 315/169.3 |

* cited by examiner

*Primary Examiner*—Hai C Pham

(57) ABSTRACT

Illumination utilizing a plurality of light sources is disclosed. In one embodiment, an illumination level is set to result in a desired contrast level. Calculations are made to derive electrical current values for each of the plurality of light sources which will illuminate a plurality of selected locations at the set illumination level.

19 Claims, 3 Drawing Sheets

ILLUMINATION UTILIZING A PLURALITY OF LIGHT SOURCES

RELATED APPLICATIONS

This patent application is related to, and claims priority from, EPO Patent application Ser. No. 04105368.7, entitled "Illumination Utilizing a Plurality of Light Sources", filed on 28 Oct. 2004, commonly assigned herewith, and hereby incorporated by reference.

BACKGROUND

In the course of performing a print job, printers periodically or continuously advance print media (e.g. paper) along a paper path. Such advancement must be made with precision; inaccuracies in the advancement will result in lessened print quality.

In some applications, one step in the advancement of the print media involves recognizing features defined on the print media, such as specific fibers which form the surface of the print media. Once recognized, a specific fiber can be used as a landmark, allowing the print media to be advanced with great precision.

However, where the print media is illuminated with poor uniformity, print media advancement which is based on recognition of features defined on the print media is impaired. For example, a feature defined on the print media may be recognized under a first lighting condition. Subsequently, the print media may be advanced to a degree that the recognized feature is located in a region having different lighting characteristics. Under the different lighting characteristics, a feature recognition module or feature recognition algorithm may be unable to locate the recognized feature. This may result in less precise control over the advancement of the print media.

Compound lighting systems, using more than one light source, have been developed in an attempt to provide more uniform lighting. However, such lighting systems have failed to provide the uniformity desired to better control the advancement of print media along the paper path in a printer. Accordingly, systems and methods which result in more uniform lighting are needed.

SUMMARY

Illumination utilizing a plurality of light sources is disclosed. In one embodiment, an illumination level is set to result in a desired contrast level. Calculations are made to derive electrical current values for each of the plurality of light sources which will illuminate a plurality of selected locations at the set illumination level.

BRIEF DESCRIPTION OF THE DRAWINGS

The following description refers to the accompanying figures. In the figures, the left-most digit(s) of a reference number identifies the figure (Fig.) in which the reference number first appears. Moreover, the same reference numbers are used throughout the drawings to reference like features and components.

DETAILED DESCRIPTION

An illumination system utilizing a plurality of light sources may be configured for operation in a variety of environments, such as an exemplary environment comprising a printer or other hard copy output device. In the printer environment, print media traveling through portions of a paper path defined through the printer is illuminated by the illumination system. Illumination of the print media promotes the successful recognition of features (such as paper fibers) defined on the print media. Such features, when recognized, can be used as landmarks when performing very precise advancements of the print media. In one embodiment, the illumination level is set to a level which results in a desired contrast level, such as a contrast level which facilitates recognition of features. Using the selected illumination level setting, calculations are made to derive electrical current values for each of the plurality of light sources which will illuminate a plurality of selected locations at the desired level. An example of the illumination system utilizing a plurality of light sources is discussed below.

Figure 1:
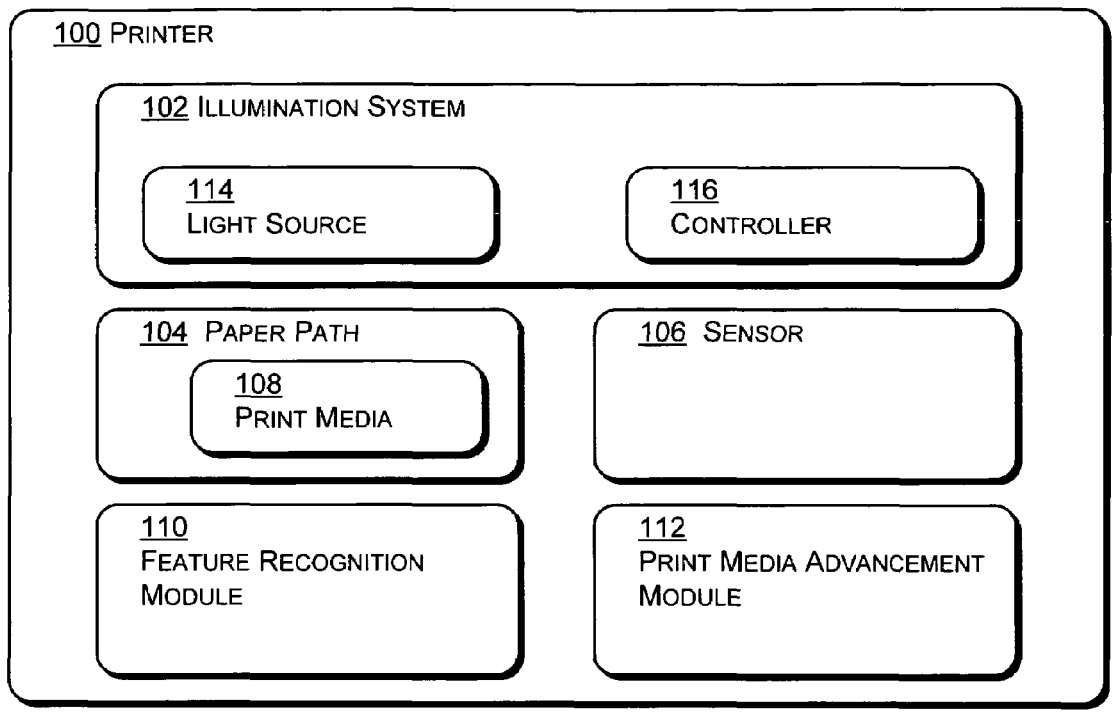
FIG. 1 is a block diagram showing an example of illumination utilizing a plurality of light sources, in this embodiment applied to a print media illumination system.

FIG. 1 is block diagram showing an example of a printer 100 within which a print media illumination system 102 is configured. The illumination system 102 illuminates portions of the paper path 104. A sensor 106 is configured to sense light received from print media 108 moving through the paper path 104. A feature recognition module 110 is configured to analyze images obtained from the sensor 106, and to thereby recognize features, such as fibers or other irregularities, present on print media 108. The location of such recognized features is utilized as an input by a print media advancement module 112. Such input is useful in moving the print media through the paper path 104 with a desired precision.

In a typical embodiment, the printer 100 may be an inkjet printer, which advances print media (e.g. sheet paper, rolled paper, envelopes, etc.) in incremental steps in a stop-and-go fashion consistent with periodic movement of a printhead across the print media. In an alternative embodiment, the printer may be a laser printer, configured to advance media in a smooth and uniform manner.

In the example of FIG. 1, the illumination system 102 includes a light source 114 and a controller 116. The illumination system 102 is configured to derive an appropriate contrast level, and then using an illumination level which resulted in the contrast level, to derive voltages to be applied to each light source included within the compound light source 114. The selected voltages should result in a desirable level of uniformity in lighting intensity between several areas of interest.

Figure 2:
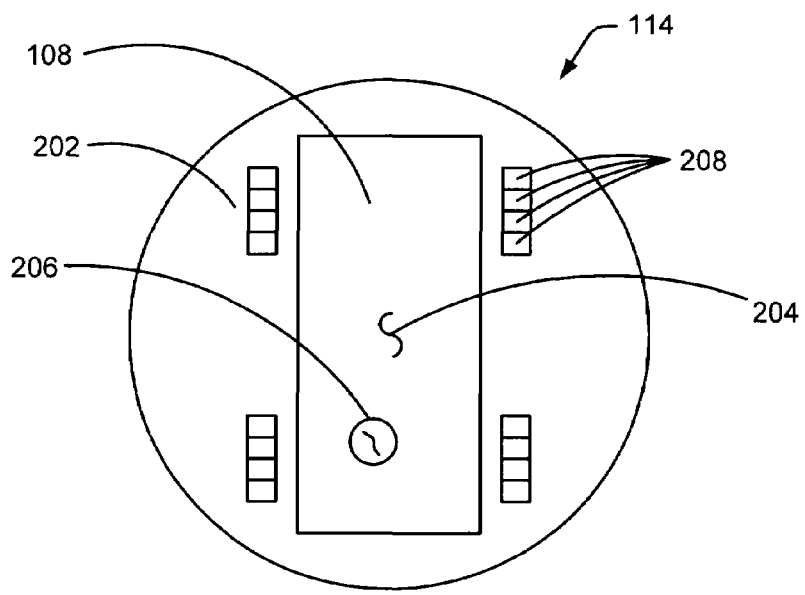
FIG. 2 is a diagram showing an example of how the plurality of lighting sources of the print media illumination system of FIG. 1 may be arranged.

The light source 114 may be based on any technology, such as LEDs, incandescent devices, florescent devices, etc. However LEDs are preferred, and will yield superior results in most applications. In FIG. 2, an example of an implementation of the light source 114 is illustrated. In this example, the light source 114 includes four LED groups 202 which are located about a hole 204 through which print media 108 may be seen. A feature 206, in this case a paper fiber enlarged to show its detail, is representative of features detectable by the sensor 106 (FIG. 1) and feature recognition module 110. In the example of FIG. 2, each LED group 202 includes four individual LEDs 208. The individual LEDs 208 within one group 202 typically receive power supplied by a single driver circuit (not shown), although each individual LED 208 could be provided with a separate current supply.

The sensor 106 (seen in FIG. 1, but removed from the view of FIG. 2 to better reveal the print media 108) is located to receive light from the light source 114 which has reflected off or otherwise received from the print media. The sensor 106 should be selected in part for the ability to monitor a region of a size greater than the amount by which the print media is periodically advanced. Accordingly, a feature identified within the region monitored by the sensor may be observable in a first position within the region before print media advancement, and in a second position within the region after advancement. As a result, the degree of the advancement may be more precisely controlled. Additionally, the sensor 106 should be selected in part for the ability to define and monitor individual pixels within the monitored region. In one example, the sensor is able to assign values within a range, such as 0 to 255, to represent gray values sensed for each pixel, within a 64 pixel by 64 pixel region.

The controller 116 may be configured as a software, firmware, hardware or hybrid module or device. For example, the controller 116 may be configured as a software procedure executed by a microcontroller, or as an application specific integrated circuit (ASIC). Additionally, the controller may include, be a part of, or be contained within, a module, such as the print media advancement module 112. The controller 116 is configured to perform a variety of functions, such as monitoring output signals from the sensor 106 and controlling the light sources 114. In one embodiment of the controller 116, its functionality is described by FIG. 3.

Figure 3:
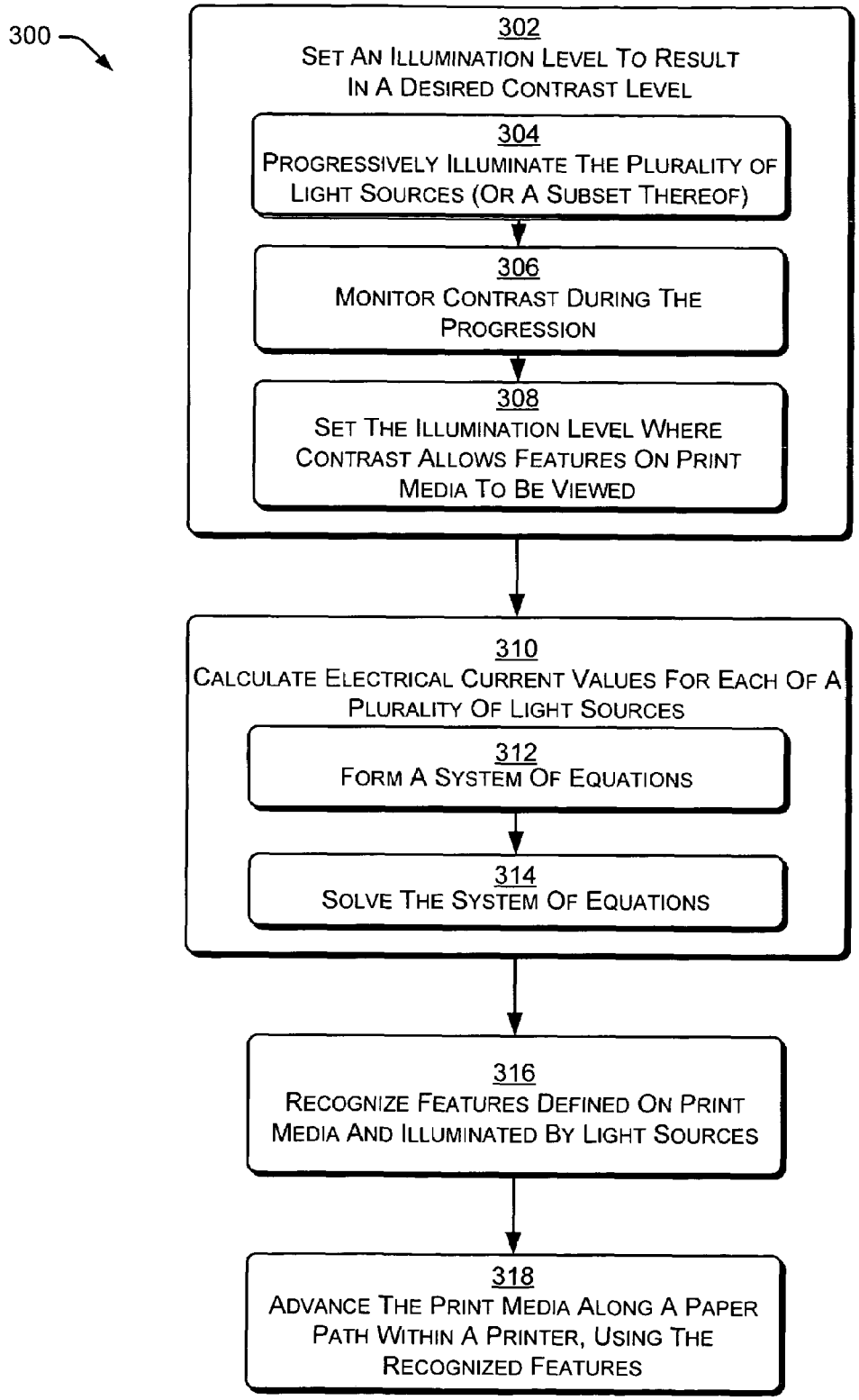
FIG. 3 is a flow diagram that describes an exemplary method to illuminate print media utilizing plural light sources.

FIG. 3 is a flow diagram that describes an exemplary method 300 to illuminate print media by utilizing a plurality of light sources. The method 300 may be implemented by controller 116 or another device, based on hardware, software or firmware. At block 302, an illumination level is set to result in a desired contrast level. In the example of FIG. 1, wherein a print system 100 is implemented, the contrast level would be based on data from the sensor 106 resulting from light reflected by or otherwise received from the print media 108. Setting the illumination level to result in a desired contrast level may be performed in a number of ways, one of which is listed here for purposes of illustration. At block 304, the light source 114 (FIG. 1) is made progressively more luminous, thereby progressively illuminating the print media 108. In one implementation, all LED groups 202 (FIG. 2) of the light source 114 are used to provide progressive levels of illumination. Optionally, the progressive illumination of the print media 108 may be repeated while using only a subset (such as half) of the LED groups 202 and/or individual LEDs 208 within the light source 114. Some media yield better contrast where, for example, only the LEDs on one side are used in the illumination. Accordingly, additional checks of the contrast using larger and smaller numbers of the available LEDs may indicate a preferred lighting strategy. The progressive illumination may be performed by incremental increases (or decreases) in the current supplied to each element within the light source 114, typically in a step-function. At block 306, contrast of an image detected by the sensor 106 is monitored for contrast during the progression.

Figure 4:
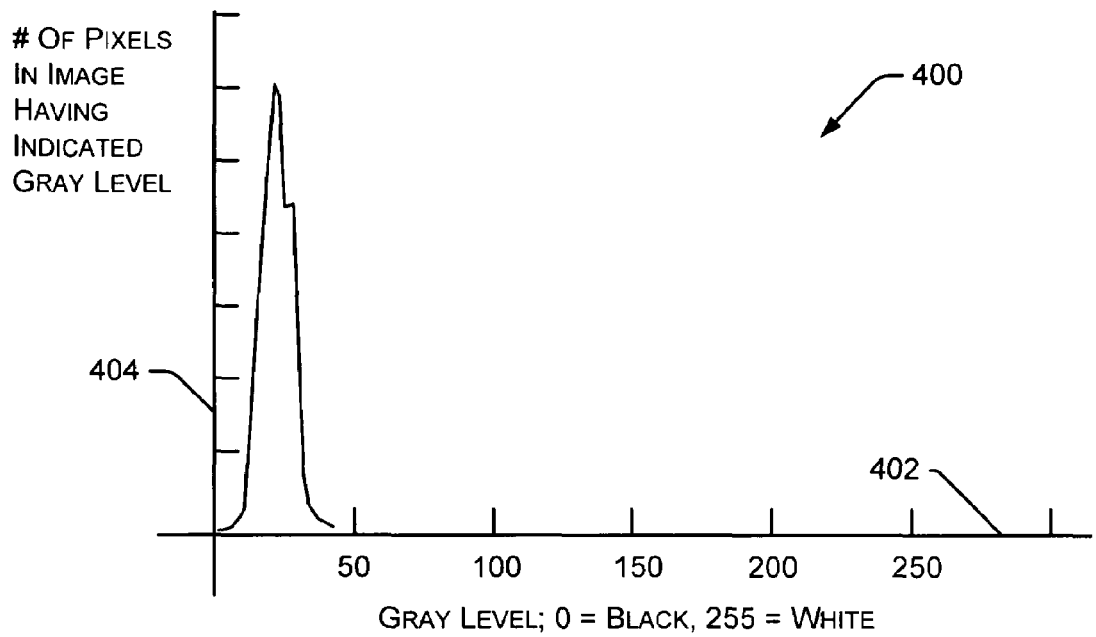
FIG. 4 and FIG. 5 show, by their comparison, that lower illumination levels result in smaller contrast levels (i.e. a smaller variance among pixels; e.g. most of the pixels are dark gray), while higher illuminations levels result in greater contrast levels (i.e. a larger variance among pixels; e.g. many lighter gray pixels mixed with darker pixels).
Figure 5:
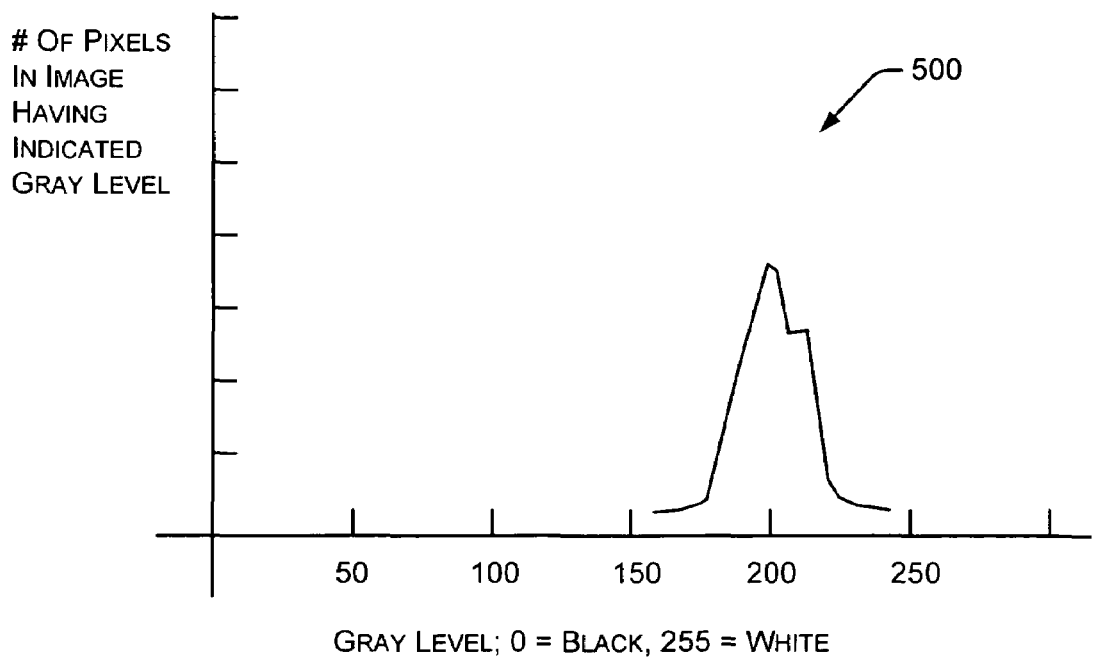

Referring to FIGS. 4 and 5, a method by which the contrast of the image detected by the sensor 106 may be monitored for contrast can be understood. FIG. 4 shows graphical information 400 obtained from the sensor 106 (FIG. 1) after viewing a portion of the print media 108 under a lower illumination level. The horizontal axis 402 is associated with gray scale values, expressed numerically from 0 (black) to 255 (white). The vertical axis 404 shows the number of pixels within the image obtained from the sensor 106 under a lower illumination level having that gray level. Accordingly, any image can be graphically represented by charting the number of pixels in the image taken by the sensor having each of the 256 gray levels. Obviously, a sensor configured to sense a different number of gray levels would result in a somewhat different graph. Referring to FIG. 4, it can be seen that at a lower illumination level, most of the pixels have approximately the same dark gray values between 0 (black) and 50 (dark gray). Accordingly, the image expresses little information, and has low contrast.

In distinction, FIG. 5 shows graphical information 500 resulting from a sensor image taken under higher illumination. In this case, the pixels in the image are spread over a larger range, wherein fewer pixels have any particular value and more pixels are distinguished from adjacent pixels. Accordingly, the image associated with the graph of FIG. 5 has more information and more contrast than the image associated with the graph of FIG. 4.

Returning to FIG. 3, block 308 shows that the illumination level can be set at a level wherein contrast is sufficient to allow features 206 (FIG. 2) on print media 108 (FIGS. 1 and 2) to be viewed. In particular, a higher level of illumination associated with a higher contrast level (such as that seen in FIG. 5) is selected, rather than a lower level of illumination which results in less contrast (such as that seen in FIG. 4).

Note that while block 302 discloses one implementation, other embodiments can also be implemented. For example, the block 302 may alternatively set the illumination level to result in a desired light intensity, or to result in a desired color light intensity.

At block 310, electrical current values for each of the plurality of light sources 114 (FIG. 1) are calculated. This may be performed in a number of ways, one of which is listed here at blocks 312-314 for purposes of illustration.

At block 312, a system of equations is formed. Typically, the system may include six to eight equations; however, this number is flexible, and could easily be adapted according to the application. Generally, the number of equations may be influenced by the number of light sources and other factors. An example of the system of equations follows:

$$SUM\_1 = (a1*Q1) + (b1*Q2) + (c1*Q3) + (d1*Q4) + \ldots$$

$$SUM\_2 = (a2*Q1) + (b2*Q2) + (c2*Q3) + (d2*Q4) + \ldots$$

$$SUM\_3 = (a3*Q1) + (b3*Q2) + (c3*Q3) + (d3*Q4) + \ldots$$

etc.

Each equation may be understood by a discussion of the first equation. In the first equation, SUM_1 represents an illumination level at a first location. The illumination level is the sum of the illumination from a plurality of groups of LEDs 202 or individual LEDs 208 which make up the light source 114 (FIG. 1). Accordingly, each equation is the sum of products, wherein each product is associated with an individual light source from within the plurality of light sources. The first location—associated with the first equation—may be a specific pixel, located on the print media 108 (FIG. 1), and represented by data contained within a location of a file which results from examination of the specific pixel by the sensor 106 (FIG. 1).

The coefficients a1, b1, c1, d1, a2, b2, c2, d2, a3, b3, c3, d3, etc. are numeric values determined by measurement during a period in which a plurality of current levels are applied to the associated light source. For example, a step-function of current values could be applied to a first light source (e.g. an element 202 or 208 within the compound light source 114) associated with current variable Q1 and the coefficient a1. The gray levels (e.g. values from 0 to 255) associated with each current level could be measured at the location associated with SUM_1. These values could then be totaled, averaged or otherwise manipulated to form the coefficient a1. Typically, the exact values of the coefficients are not important; instead, it is their relative size that is important. Therefore, by deriving each coefficient in a similar manner, based on measurements associated with the location associated with the equation and the light source associated with the term of the coefficient, appropriate coefficients will be derived. Accordingly, coefficient b1 could be determined by stepping current values through a second light source associated with the variable Q2, with measurements taken at the location (e.g. a pixel within the image of the sensor) associated with SUM_1. And similarly, coefficient d3 could be found in a manner similar to coefficient a1, but with measurements taken at the location associated with SUM_3 while current was stepped through light source 4 associated with current variable Q4.

Note that the locations within the image taken by the sensor 106 are typically distributed somewhat evenly through the image, and that while six or eight locations may be typical, a greater or lesser number of locations (and therefore equations) could be selected.

Prior to solving the equations, the values for SUM_1, SUM_2 and SUM_3, etc. are set to a value which resulted in the desired contrast (see block 302). For example, if the sensor 106 measures gray on a scale of zero to 255, the desired contrast may be (as illustrated in FIG. 5) around 200. Thus, the values for SUM_1, SUM_2 and SUM_3, etc. could be set to 200.

At block 314, the system of equations is solved. Note that the number of equations and unknowns may not be equal. Thus, the system could be over-constrained or under-constrained, i.e. there could be more or less equations than variables (the Q's). However, it is generally best to have fewer locations (that is fewer equations, since each SUM_x is associated with a location) than there are light sources (i.e. the Q's). This allows more flexibility in the solution to the equations; that is, one or more values for Q can be arbitrarily set, and the others derived. For example, in most applications the solution is more stable if one of the currents is forced to the level of maximum contrast.

At block 316, features 204 (FIG. 2) defined on the print media 108 (FIGS. 1 and 2) and illuminated by the light sources 114 are recognized. Features are typically fibers, which form the paper of the print media. Recognition of a feature 204 provides a "landmark" on the print media, which helps to advance the print media by a precise amount. Accordingly, at block 318 the print media is advanced along a paper path within a printer, using the recognized feature(s). Note that blocks 316 and 318 may be repeated more frequently, while the earlier blocks may be repeated only upon loading the media or upon changing the media.

In general, the process 300 of FIG. 3 is performed whenever new print media is used. For example, where different print media is located in different trays within the printer, and frequent changes of print media are performed, it is advisable to reset the illumination level (e.g. block 302) and recalculate the current levels (e.g. block 310). Such calculations should additionally be performed at intervals due to LED replacement or aging. However, these events typically occur much more infrequently than changes in print media.

Although the above disclosure has been described in language specific to structural features and/or methodological steps, it is to be understood that the appended claims are not limited to the specific features or steps described. Rather, the specific features and steps are exemplary forms by which this disclosure may be implemented. For example, while actions described in blocks of the flow diagrams may be performed in parallel with actions described in other blocks, the actions may occur in an alternate order, or may be distributed in a manner which associates actions with more than one other block. And further, while elements of the methods disclosed are intended to be performed in any desired manner, it is anticipated that computer- or processor-readable instructions, performed by a computer and/or processor, typically located within a printer, reading from a computer- or processor-readable media, such as a ROM, disk or CD ROM, would be preferred, but that an application specific gate array (ASIC) or similar hardware structure, could be substituted.

The invention claimed is:

1. A method of illumination utilizing a plurality of light sources, comprising:
    setting an illumination level;
    calculating electrical current values for each of the plurality of light sources to illuminate a plurality of selected locations at the set illumination level;
    recognizing print media features illuminated by the plurality of light sources;
    advancing the print media along a printer paper path within a printer; and
    identifying the print media features observable within a region monitored by a sensor and being observable in a first position within the region before print media advancement and in a second position within the region after advancement.

2. The method of claim 1, wherein setting the illumination level comprises:
    setting the illumination level to result in a desired contrast level.

3. The method of claim 1, wherein setting the illumination level comprises:
    setting the illumination level to result in a desired light intensity level.

4. The method of claim 1, wherein setting the illumination level comprises:
    setting the illumination to control color light intensity.

5. The method of claim 1, wherein setting the illumination level comprises:
    progressively illuminating the plurality of light sources;
    monitoring contrast during the progression; and
    setting the illumination level where the contrast is sufficient to view features on print media.

6. The method of claim 5, wherein progressively illuminating the plurality of light sources comprises:
    performing the progressive illumination with a subset of the plurality of light sources.

7. The method of claim 1, wherein calculating electrical current values comprises:
    forming a system of equations, wherein each equation within the system equates an illumination level with a sum of products, wherein each product within the sum comprises:
        a coefficient derived by measuring light levels over a range of currents supplied to an element within the plurality of light sources; and a variable corresponding to a current level applied to the element within the plurality of light sources; and solving the system of equations for the variables to establish current levels for each of the plurality of light sources.

8. The method of claim 1, wherein calculating electrical current values comprises:

forming a system of equations, wherein each equation is formed according to:

the illumination level=a1*Q1+b1*Q2+. . . , where a1 and b1 comprise numeric values determined by measurement during a period in which a plurality of current levels are applied to the plurality of light sources, and where Q1 and Q2 comprise variables; and solving the system of equations for the variables to establish current levels for each of the plurality of light sources.

9. The method of claim 1, wherein calculating electrical current values comprises:

forming a system of equations wherein:

each equation is associated with a location observed by a sensor;

each equation is set equal to the illumination level;

a coefficient in each term is derived from measured light levels resulting from operation of a light source at a plurality of input currents; and a variable in each term is associated with current levels in the light source; and solving the system of equations for the variables to establish current levels for each of the plurality of light sources.

10. An illumination system, comprising:

a plurality of light sources;

a sensor, configured to sense illumination emitted from the plurality of light sources; and a controller configured for:

setting an illumination level to result in a desired contrast level by;

progressively illuminating the plurality of light sources;

monitoring contrast at intervals during the progression; and setting the illumination level where the contrast is sufficient to view features on print media; and calculating electrical current values for each of the plurality of light sources to illuminate a plurality of selected locations at the illumination level.

11. The illumination system of claim 10, wherein the plurality of light sources comprises:

a plurality of grouped light sources; and a plurality of LEDs within each of the plurality of grouped light sources.

12. The illumination system of claim 10, wherein the sensor is configured to monitor a region of pixels on print media greater than a number of pixels by which the print media is periodically advanced by a printing device.

13. The illumination system of claim 10, wherein the sensor is configured to monitor a region of pixels large enough to distinguish between different contrast levels associated with different illumination levels.

14. The illumination system of claim 10, wherein calculating electrical current values comprises:

forming a system of equations, wherein each equation within the system equates an illumination level with a sum of products, wherein each product within the sum comprises:

a coefficient derived by measuring light levels over a range of currents supplied to an element within the plurality of light sources; and a variable corresponding to a current level applied to the element within the plurality of light sources; and solving the system of equations for the variables to establish current levels for each of the plurality of light sources.

15. The illumination system of claim 10, wherein calculating electrical current values comprises:

forming a system of equations in a form: the illumination level=a1*Q1+b1* Q2+. . . , where a1 and b1 comprise numeric values determined by measurement during a period in which a plurality of current levels are applied to the plurality of light sources, and where Q1 and Q2 comprise variables; and solving the system of equations for the variables to establish current levels for each of the plurality of light sources.

16. The illumination system of claim 10, wherein calculating electrical current values comprises:

forming a system of equations wherein:

each equation is associated with a location observed by the sensor;

each equation is set equal to the illumination level;

a coefficient derived by measuring light levels over a range of currents supplied to an element within the plurality of light sources; and a variable corresponding to a current level applied to the element within the plurality of light sources; and solving the system of equations for the variables to establish current levels for each of the plurality of light sources.

17. The illumination system of claim 10, additionally comprising:

a feature recognition module to recognize features defined on print media and illuminated by the plurality of light sources; and a print media advancement mechanism, to advance print media along a paper path within a printer, using the recognized features.

18. A method of illumination utilizing a plurality of light sources, comprising:

recognizing features defined on a print media and illuminated by the plurality of light sources;

advancing the print media along a printer paper path within a printer; and identifying the print media features observable within a region monitored by a sensor and being observable in a first position within the region before print media advancement and in a second position within the region after advancement;

progressively illuminating the plurality of light sources;

monitoring contrast at intervals during the progression; and setting the illumination level where the contrast is sufficient to view the print media features.

19. A processor-readable medium comprising processor-executable instructions for illuminating print media, the processor-executable instructions comprising instructions adapted to implement the method of claim 18.

* * * * *